(12) United States Patent
Charbit

(10) Patent No.: US 10,016,348 B2
(45) Date of Patent: Jul. 10, 2018

(54) TWO-PHASE COMPOSITION COMPRISING A FATTY ACID ESTER OF SUGAR OR A LIQUID ALKYL POLYGLUCOSIDE, WITH AN HLB < 8, AND A $C_8$-$C_{18}$ BRANCHED ALKANE

(71) Applicant: L'OREAL, Paris (FR)

(72) Inventor: Yael Charbit, Vitry-sur-Seine (FR)

(73) Assignee: L'OREAL, Paris (FR)

( * ) Notice: Subject to any disclaimer, the term of this patent is extended or adjusted under 35 U.S.C. 154(b) by 68 days.

(21) Appl. No.: 15/033,196

(22) PCT Filed: Oct. 24, 2014

(86) PCT No.: PCT/EP2014/072907
§ 371 (c)(1),
(2) Date: Apr. 29, 2016

(87) PCT Pub. No.: WO2015/062993
PCT Pub. Date: May 7, 2015

(65) Prior Publication Data
US 2016/0256367 A1    Sep. 8, 2016

(30) Foreign Application Priority Data
Oct. 29, 2013    (FR) ..................... 13 60530

(51) Int. Cl.
| | |
|---|---|
| *C11D 3/22* | (2006.01) |
| *A61K 8/03* | (2006.01) |
| *A61K 8/31* | (2006.01) |
| *A61Q 1/14* | (2006.01) |
| *A61Q 19/00* | (2006.01) |
| *A61K 8/60* | (2006.01) |
| *A61Q 19/10* | (2006.01) |
| *A61K 8/34* | (2006.01) |
| *A61Q 13/00* | (2006.01) |

(52) U.S. Cl.
CPC .................. *A61K 8/31* (2013.01); *A61K 8/03* (2013.01); *A61K 8/342* (2013.01); *A61K 8/345* (2013.01); *A61K 8/60* (2013.01); *A61K 8/602* (2013.01); *A61K 8/604* (2013.01); *A61Q 1/14* (2013.01); *A61Q 13/00* (2013.01); *A61Q 19/10* (2013.01); *A61K 2800/262* (2013.01); *A61K 2800/34* (2013.01); *A61K 2800/49* (2013.01); *A61K 2800/591* (2013.01)

(58) Field of Classification Search
CPC ........... C11D 1/662; C11D 3/182; C11D 3/22; C11D 7/242; A61K 8/03; A61K 8/31; A61K 8/602; A61K 8/604; A61Q 1/14; A61Q 19/00
See application file for complete search history.

(56) References Cited

U.S. PATENT DOCUMENTS

| | | | |
|---|---|---|---|
| 5,871,758 A | 2/1999 | Nagy et al. | |
| 6,297,204 B1 * | 10/2001 | Picard | A61K 8/03 510/119 |

FOREIGN PATENT DOCUMENTS

| | | | | |
|---|---|---|---|---|
| DE | 199 45 503 A1 | 4/2001 | | |
| WO | WO 2014/013420 | * | 1/2014 | ............... A61K 8/37 |
| WO | WO-2014/013420 A2 | 1/2014 | | |

* cited by examiner

*Primary Examiner* — Brian P Mruk
(74) *Attorney, Agent, or Firm* — Polsinelli PC

(57) ABSTRACT

The present invention relates to a composition for topical application consisting of an aqueous phase and an oily phase, which are separate and transparent, comprising at least one surfactant that is liquid at room temperature and at atmospheric pressure, with an HLB<8 and chosen from fatty acid esters of sugar and alkyl polyglucosides, at least one branched alkane comprising from 8 to 18 carbon atoms, and from 0 to 4% by weight of silicone oils relative to the total weight of the composition.

The composition according to the invention makes it possible to obtain, after shaking, an emulsion that rapidly separates again into two transparent phases, having a perfectly sharp interface and with no appearance of droplets that remain attached to the walls of the transparent container. The composition in accordance with the invention has the same makeup-removing efficacy and better sensory properties, and in particular it leaves less greasy residue on the skin.

20 Claims, No Drawings

TWO-PHASE COMPOSITION COMPRISING A FATTY ACID ESTER OF SUGAR OR A LIQUID ALKYL POLYGLUCOSIDE, WITH AN HLB < 8, AND A $C_8$-$C_{18}$ BRANCHED ALKANE

CROSS REFERENCE TO RELATED APPLICATIONS

This application is a National Phase filing under 35 U.S.C. § 371 of PCT/EP2014/072907 filed on Oct. 24, 2014; and this application claims priority to Application No. 1360530 filed in France on Oct. 29, 2013 under 35 U.S.C. § 119. The entire contents of each application are hereby incorporated by reference.

The present invention relates to a composition for topical application, consisting of two separate phases, an aqueous phase and an oily phase, which emulsify readily by shaking and which undergo rapid phase separation after the shaking is stopped. The present invention also relates to the use of the said composition in cosmetics or dermatology, and especially for removing makeup from, cleansing and/or caring for the skin, both bodily and facial skin, and in particular the lips and/or the eyes, and/or for haircare.

Compositions of this type consisting of two separate phases, especially an aqueous phase and an oily phase which are separate and not emulsified one in the other at rest, are generally referred to as "two-phase compositions". They differ from emulsions in that when at rest, the two phases are separate instead of being emulsified one in the other. Thus, the two phases are separated at rest by a single interface, whereas, in emulsions, one of the phases is dispersed in the other in the form of a multitude of droplets, and the interfaces are therefore multiple, these interfaces generally being stabilized with emulsifying surfactants and/or emulsifying polymers. The use of two-phase compositions necessitates prior shaking in order to form an extemporaneous emulsion. This emulsion must be of sufficient quality and stability to enable homogeneous application of the two phases, but such that when at rest, the two phases become rapidly separated and regain their initial state, this phenomenon being more commonly known as "phase separation".

Rapid phase separation (or demixing) of the two phases after their use is one of the desired qualities of two-phase compositions. Specifically, obtaining rapid phase separation is desirable for various reasons, especially since poor separation of the two phases is perceived by users as being unaesthetic.

In addition, it is increasingly sought to have clear, i.e. transparent, compositions, since, as in the case of water, transparency is a symbol of purity and thus of cleanliness. Transparent compositions are thus particularly appreciated by users, these compositions are generally presented in transparent containers, and the opacity of the two phases is aesthetically detrimental.

The use, in two-phase compositions, of silicone oils such as cyclopentasiloxane, for example, in a suitable amount may make it possible to obtain two-phase compositions consisting of two separate immiscible phases which form, after shaking, an emulsion, while keeping the desired properties for the two-phase compositions, i.e. rapid phase separation into two transparent phases.

Two-phase compositions based on cyclic silicone oils have already been described, for example in documents EP 0 370 856 and EP 0 603 080, especially for removing eye makeup.

Moreover, consumers are increasingly in search of cosmetic products formed on the basis of natural constituents or constituents of natural origin, in particular products not comprising any volatile silicone compounds.

Document FR 2 939 662 especially proposes two-phase compositions based on non-silicone oils consisting of two separate immiscible phases which form, after shaking, an emulsion, while keeping the desired properties for the two-phase compositions, i.e. rapid phase separation into two transparent phases with a sharp interface.

However, depending on the non-silicone oils used, small droplets may form, which remain attached to the walls of the transparent container, both for the aqueous phase and for the fatty phase. This phenomenon is visually unacceptable.

There is thus a need for a two-phase composition consisting of two separate immiscible phases, comprising little or no silicone compound, which, after shaking, gives an emulsion, while keeping the desired properties for the two-phase compositions, i.e. rapid phase separation into two transparent phases, a sharp interface after returning to rest, without the appearance of droplets that remain attached to the walls of the transparent container. Surprisingly, the Applicant has found that it is possible to obtain a transparent two-phase composition comprising little or no silicone compound, which, after shaking, gives an emulsion and which undergoes phase separation again rapidly into two transparent phases, having a perfectly sharp interface and without the appearance of droplets that remain attached to the walls of the transparent container, by using a combination of a branched alkane comprising from 8 to 18 carbon atoms and a surfactant that is liquid at room temperature (20-25° C.) and at atmospheric pressure, with an HLB<8 and chosen from sugar derivatives.

More particularly, a subject of the invention is a composition consisting of an aqueous phase and an oily phase, which are separate and transparent, comprising at least one surfactant that is liquid at room temperature (20-25° C.) and at atmospheric pressure (760 mmHg or $1.013 \times 10^5$ Pa), with an HLB<8 and chosen from fatty acid esters of sugar and alkyl polyglucosides, at least one branched alkane comprising from 8 to 18 carbon atoms, and from 0 to 4% by weight of silicone oils relative to the total weight of the composition. The composition in accordance with the invention has the same makeup-removing efficacy and better sensory properties, and in particular it leaves less greasy residue on the skin. Since the composition according to the invention is intended for topical application, it contains a physiologically acceptable medium, i.e. a medium that is compatible with the skin, mucous membranes, the hair and the scalp.

The composition according to the invention comprises at least an aqueous phase and an oily phase which are separate. These two phases are separate, i.e. they are visible one above the other at rest, and the interface between the two is perfectly sharp. They are transparent at rest, and when the composition is shaken before use, the mixture obtained consists of the emulsion of one phase in the other. The two phases may or may not be coloured.

In the text hereinbelow, the expression "at least one" is equivalent to "one or more" and, unless otherwise indicated, the limits of a range of values are included in that range.

The word "transparent" means that the phase has a turbidity of less than or equal to 300 NTU. The transparency of a composition may be measured by its turbidity, and the NTU (nephelometric turbidity units) are the units for measuring the turbidity of a composition. The turbidity measurement may be performed, for example, with a model 2100P turbidimeter from the Hach Company, the tubes used for the measurement being referenced AR397A cat 24347-06. The measurements are performed at room temperature (20° C. to 25° C.). The two separate phases of the composition in accordance with the invention have a turbidity generally ranging from 0.1 to 300 NTU and preferably from 1 to 100 NTU.

Aqueous Phase

The aqueous (or hydrophilic) phase of the composition according to the invention advantageously comprises water.

The amount of aqueous phase may range from 50% to 80% by weight and preferably from 55% to 70% by weight relative to the total weight of the composition. The amount of water can represent all or part of the aqueous phase and it is generally at least 50% by weight relative to the total weight of the composition.

The water used may be sterile demineralized water and/or a floral water such as rose water, cornflower water, chamomile water or lime blossom water, and/or a natural spring water or mineral water, for instance: Vittel water, Vichy basin water, Uriage water, Roche Posay water, Bourboule water, Enghien-les-Bains water, Saint Gervais-les-Bains water, Néris-les-Bains water, Allevar-les-Bains water, Digne water, Maizières water, Neyrac-les-Bains water, Lons-le-Saunier water, Eaux Bonnes water, Rochefort water, Saint Christau water, Fumades water, Tercis-les-bains water and Avene water. The aqueous phase may also comprise reconstituted spring water, i.e. a water containing trace elements such as zinc, copper, magnesium, etc., reconstituting the characteristics of a spring water.

The aqueous (or hydrophilic) phase of the composition according to the invention may also contain any water-soluble or water-dispersible additive. Water-soluble additives that may especially be mentioned are polyols comprising from 2 to 8 carbon atoms. The term "polyol" should be understood as meaning any organic molecule comprising at least two free hydroxyl groups. Examples of polyols that may be mentioned include glycerol, glycols, for instance butylene glycol, propylene glycol, isoprene glycol, dipropylene glycol, hexylene glycol, polyethylene glycols and polypropylene glycol. According to a particular embodiment of the invention, the polyol is chosen from glycerol and hexylene glycol. Preferably, the polyol is hexylene glycol.

The polyols may be present in the composition according to the invention in a content ranging from 0.1% to 60% by weight, preferably from 0.5% to 50%, better still from 2% to 30% by weight and even better still from 3% to 20% by weight relative to the total weight of the composition.

Water-soluble additives that may also be mentioned include primary alcohols, i.e. an alcohol comprising from 1 to 6 carbon atoms, such as ethanol and isopropanol. It is preferably ethanol. This alcohol may be present in an amount that is, for example, less than or equal to 40% by weight and preferably ranging from 0.1% to 20% by weight relative to the total weight of the composition. The addition of such an alcohol may especially be suitable when the composition according to the invention is used as a product for the body or the hair.

Oily Phase

The oily phase generally represents from 20% to 50%, preferably from 25% to 45% by weight, and better still from 30% to 40% by weight relative to the total weight of the composition.

The oily phase of the composition according to the invention comprises at least one branched alkane comprising from 8 to 18 carbon atoms and preferably from 12 to 16 carbon atoms.

According to a particular embodiment, the branched alkane(s) comprising from 8 to 18 carbon atoms are chosen from $C_8$-$C_{18}$ isoalkanes (also known as isoparaffins), such as isododecane, isodecane or isohexadecane, for example the isoparaffins sold under the trade name Isopar by the company Exxon Chemical or the oils sold under the trade name Permethyl by the company Presperse, and the isohexadecane and isododecane sold by the company Ineos.

According to a particular embodiment of the invention, the branched alkane(s) comprising from 8 to 18 carbon atoms are present in the composition in an amount at least equal to 40% by weight and preferably between 45% and 100% by weight relative to the total weight of the oily phase.

Moreover, the composition according to the invention comprises less than 4% by weight of silicone oils relative to the total weight of the composition, preferably less than 3%, more preferably less than 2%, better still less than 1% by weight and even better still less than 0.5% by weight of silicone oils. Preferably, the composition in accordance with the invention is free of silicone oils.

The term "silicone oil" means an oil containing at least one silicon atom, and especially containing Si—O groups.

Examples of silicone oils that may be mentioned include volatile silicone oils such as cyclopolydimethylsiloxanes (INCI name: cyclomethicone), such as cyclopentasiloxane, cyclohexasiloxane, octamethylcyclotetrasiloxane, decamethylcyclopentasiloxane, dodecamethylcyclohexasiloxane; linear silicones such as heptamethylhexyltrisiloxane, heptamethyloctyltrisiloxane, hexamethyldisiloxane, octamethyltrisiloxane, decamethyltetrasiloxane or dodecamethylpentasiloxane; non-volatile silicone oils such as polymethylsiloxanes (PDMS), and phenyl polymethylsiloxanes such as phenyl trimethicones, phenyl dimethicones, phenyltrimethylsiloxydiphenylsiloxanes, diphenyl dimethicones, diphenylmethyldiphenyltrisiloxanes, 2-phenylethyl trimethyl siloxysilicates and polymethylphenylsiloxanes; polysiloxanes modified with fatty acids, fatty alcohols or polyoxyalkylenes, and mixtures thereof.

The composition according to the invention may also comprise at least one additional non-silicone oil other than the branched alkanes comprising from 8 to 18 carbon atoms. The additional non-silicone oil(s) may be chosen from volatile or non-volatile hydrocarbon-based oils other than the branched alkanes comprising from 8 to 18 carbon atoms.

The term "hydrocarbon-based oil" means an oil formed essentially from, or even consisting of, carbon and hydrogen atoms, and possibly oxygen and nitrogen atoms, and containing no silicon or fluorine atoms; it may contain ester, ether, amine or amide groups.

The term "volatile" refers to a compound that can evaporate on contact with the skin in less than one hour, at room temperature and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

Examples of non-silicone oils that may be used in the composition of the invention include:
  hydrocarbon-based oils of plant origin, such as perhydrosqualene, liquid triglycerides of fatty acids comprising from 4 to 10 carbon atoms, such as heptanoic or octanoic acid triglycerides, or alternatively, for example, sunflower oil, maize oil, soybean oil, marrow oil, grapeseed oil, sesame seed oil, hazelnut oil, apricot kernel oil, macadamia oil, arara oil, coriander oil, castor oil, avocado oil, caprylic/capric acid triglycerides, such as those sold by the company Stearineries Dubois or those sold under the names Miglyol 810, 812 and 818 by the company Dynamit Nobel, jojoba oil and shea butter oil;

synthetic esters and ethers, especially of fatty acids and/or of fatty alcohols, for instance the oils of formulae $R^1COOR^2$ and $R^1OR^2$ in which $R^1$ represents a fatty acid residue containing from 7 to 29 carbon atoms and $R^2$ represents a branched or unbranched hydrocarbon-based chain containing from 3 to 30 carbon atoms, for instance purcellin oil, isononyl isononanoate, isopropyl myristate, isopropyl palmitate, 2-ethylhexyl palmitate, 2-octyldodecyl stearate, isocetyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

volatile or non-volatile, linear or branched hydrocarbons, of mineral or synthetic origin, and derivatives thereof, other than the branched alkanes comprising from 8 to 18 carbon atoms, such as liquid petroleum jelly and hydrogenated polyisobutene such as Parleam® oil; volatile linear alkanes comprising from 7 to 17 carbon atoms such as undecane or tridecane;

fatty alcohols that are liquid at room temperature, containing from 8 to 26 carbon atoms, for instance octyldodecanol, 2-butyloctanol, 2-hexyldecanol, 2-undecylpentadecanol or oleyl alcohol.

According to a particular embodiment of the invention, the composition comprises at least one additional non-silicone oil chosen from the following hydrocarbon-based oils:

fatty acid esters comprising from 8 to 30 carbon atoms, such as isodecyl neopentanoate, isopropyl myristate, isopropyl palmitate, 2-ethylhexyl palmitate, 2-octyldodecyl stearate or isocetyl stearate; linear hydrocarbons such as Parleam® oil and liquid petroleum jelly, volatile linear alkanes comprising from 7 to 17 carbon atoms such as undecane or tridecane. Among the volatile linear alkanes comprising from 7 to 17 carbon atoms, in particular from 9 to 15 carbon atoms and more particularly from 11 to 13 carbon atoms, mention may be made of alkanes such as those that are described in the Cognis patent applications WO 2007/068 371 or WO 2008/155 059 (mixtures of different alkanes differing by at least one carbon). These alkanes are obtained from fatty alcohols, which are themselves obtained from coconut oil or palm oil.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13) and n-tetradecane (C14), and mixtures thereof. According to a particular embodiment, the volatile linear alkane is chosen from n-nonane, n-undecane, n-dodecane, n-tridecane and n-tetradecane, and mixtures thereof. According to one preferred embodiment, mention may be made of mixtures of n-undecane (C11) and of n-tridecane (C13) obtained in Examples 1 and 2 of patent application WO 2008/155 059 by the company Cognis.

According to another particular embodiment of the invention, the composition does not comprise any additional non-silicone oil. In this embodiment, the composition comprises only oils chosen from branched alkanes comprising from 8 to 18 carbon atoms, alone or as a mixture.

In the composition of the invention, all oils taken together, the total amount of oil(s) may range, for example, from 20% to 50% by weight and preferably from 30% to 45% by weight relative to the total weight of the composition, and the total amount of volatile oils may range, for example, from 0 to 50% by weight, preferably from 5% to 40% by weight and better still from 5% to 30% by weight relative to the total weight of the composition.

According to a particular embodiment of the invention, the weight ratio between the aqueous phase and the oily phase ranges from 55/45 to 80/20 and better still from 50/50 to 70/30.

This weight ratio is adjusted according to the desired cosmeticity and so that the composition has a freezing point of less than 4° C.

Surfactants

The composition according to the invention comprises at least one surfactant that is liquid at room temperature (20-25° C.) and at atmospheric pressure (760 mmHg or $1.013 \times 10^5$ Pa), with an HLB<8 and chosen from fatty acid esters of sugar and alkyl polyglucosides. The term "HLB" is well known to those skilled in the art, and denotes the hydrophilic-lipophilic balance of a surfactant. The HLB or hydrophilic-lipophilic balance of the surfactant(s) used according to the invention may be determined via the Griffin method or the Davies method.

The scale ranges from 0 to 20 (limits exclusive, otherwise the molecules are no longer surfactants). The higher the value, the greater the solubility in water, and vice versa, the lower the value, the greater the affinity of the surfactant for oil.

The Griffin HLB value is defined in the publication *J. Soc. Cosm. Chem.* 1954 (Vol 5), pages 249-256 or the HLB determined experimentally and as described in the publication from the authors F. Puisieux and M. Seiller, entitled Galenica 5: Les systèmes dispersés—Tome I—Agents de surface et émulsions—Chapitre IV—Notions de HLB et de HLB critique, pages 153-194—paragraphe 1.1.2. Détermination de HLB par voie expérimentale [Experimental determination of HLB], pages 164-180.

It is preferably the calculated HLB values that should be taken into account.

The calculated HLB is defined as being the following coefficient:

calculated HLB=20×molar mass of the hydrophilic part/total molar mass.

The Davies HLB consists in summing up the hydrophilic and lipophilic contributions made by each of the structural groups of the surfactant:

$$HLB = \Sigma HLB_{hydrophilic\ groups} - HLB_{hydrophobic\ groups} + 7$$

Thus, the HLB of the surfactant is equal to the sum of the HLB values of the hydrophilic groups minus the sum of the HLB values of the hydrophobic groups plus 7.

HLB tables exist for the various standard groups, which may be found especially in the following treatise: Surfactants in Cosmetics, second edition, surfactant science series volume 68, edited by Martin M. Rieger & Linda D. Rhein, p. 134, table 4.

According to a particular embodiment of the invention, the surfactant(s) that are liquid at room temperature and at atmospheric pressure, with an HLB<8 comprise one or more linear or branched, saturated or unsaturated hydrocarbon-based chains, comprising from 11 to 44 carbon atoms, preferably from 12 to 24 carbon atoms, even more preferentially from 16 to 22 carbon atoms and better still from 18 to 20 carbon atoms.

The term "hydrocarbon-based chain" means a group formed essentially from, or even consisting of, carbon and hydrogen atoms, and possibly oxygen and nitrogen atoms, and not containing any silicon or fluorine atoms; it may contain ester, ether, amine or amide groups.

Fatty Acid Esters of Sugar

The fatty acid ester(s) of sugar may be monoesters or polyesters of a fatty acid and of a sugar or of an alkyl sugar. They may be oxyalkylenated, for example oxyethylenated and/or oxypropylenated, or polyglycerolated.

They may be chosen especially from the group comprising esters or mixtures of esters of C11-C22 and preferably C12-C20 fatty acids, optionally with one or more unsaturations, and of sucrose (saccharose), maltose, glucose, fructose or xylose, and esters or mixtures of esters of C11-C22 and preferably C12-C20 fatty acids, optionally with one or more unsaturations, and of ($C_1$-$C_4$ alkyl)glucose, such as methylglucose, and mixtures thereof. According to a particular embodiment, the C11-C22 (preferably C12-C20, even more preferentially C14-C20 and better still C16-C18) fatty acids forming the fatty unit of the esters that may be used according to the invention comprise a linear or branched, saturated or unsaturated hydrocarbon-based chain, comprising from 11 to 22 carbon atoms (preferably from 12 to 20 carbon atoms, even more preferentially from 14 to 20 carbon atoms and better still from 16 to 18 carbon atoms). The fatty unit of the esters may be chosen especially from stearates, behenates, cocoates, arachidonates, palmitates, myristates, laurates, caprates and oleates, and mixtures thereof. Oleates are preferably used.

According to another particular embodiment, the sugar unit of the fatty acid ester(s) of sugar may comprise a C1-C4 alkyl group. It is chosen, for example, from sucrose, maltose, glucose, fructose, mannose, galactose, arabinose, xylose, lactose, trehalose and methylglucose. Sucrose, glucose and methylglucose are preferably used, and even more preferentially methylglucose.

According to a preferred embodiment of the invention, the C11-C22 (preferably C12-C20, even more preferentially C14-C20 and better still C16-C18) fatty acids forming the fatty unit of the esters that may be used according to the invention comprise an unsaturated linear hydrocarbon-based chain, comprising from 11 to 22 carbon atoms (preferably from 12 to 20, even more preferentially from 14 to 20 and better still from 16 to 18).

According to a preferred embodiment, the fatty acid ester(s) of sugar result from the reaction of a fatty acid whose fatty unit comprises an unsaturated linear hydrocarbon-based chain comprising from 12 to 24 carbon atoms and preferably from 16 to 20 carbon atoms, and of a ($C_1$-$C_4$ alkyl) sugar.

Preferably, the fatty acid ester(s) of sugar are diesters.

In particular, the fatty acid ester of sugar is chosen from methylglucose dioleate.

An example of a methylglucose dioleate that may be mentioned is the product sold under the name Glucate DO Emulsifier by the company Lubrizol, the HLB value of which, calculated via the Davies method, is equal to −1.275.

Alkyl Polyglucosides

The alkyl polyglucoside(s) used in the context of the invention may or may not be polyalkoxylated.

According to a particular embodiment, they are chosen from the compounds having the following general formula:

$$RO-(G)_a$$

in which R denotes a saturated or unsaturated, linear or branched hydrocarbon-based chain, comprising from 12 to 44 carbon atoms, the group G denotes a saccharide residue comprising from 5 to 6 carbon atoms and a is a number ranging from 1 to 10, preferably from 1 to 5 and even more preferentially a is equal to 1.

According to a particular embodiment, R denotes a branched alkyl radical comprising from 12 to 44 carbon atoms, preferably from 16 to 36 carbon atoms and better still from 18 to 22 carbon atoms.

According to another particular embodiment, the saccharide residue is chosen from glucose, dextrose, saccharose, fructose, galactose, maltose, maltotriose, lactose, cellobiose, mannose, ribose, dextran, talose, allose, xylose, levoglucan, cellulose, starch and methylglucose. More preferentially, the saccharide residue denotes xylose.

The alkyl polyglucoside(s) may be chosen especially from the group comprising ethers or mixtures of ethers of fatty alcohols comprising from 12 to 44 carbon atoms and of glucose, maltose, sucrose, xylose or fructose, and ethers or mixtures of ethers of fatty alcohols comprising from 12 to 44 carbon atoms and of methylglucose.

The fatty unit of the ethers may be chosen especially from cetyl, behenyl, arachidyl, stearyl, palmityl, myristyl, lauryl, hexadecanoyl and octyldodecyl units, and mixtures thereof such as cetearyl. Preferably, it is octyldodecyl.

According to a particular embodiment of the invention, the alkyl polyglucoside(s) are chosen from the compounds having the following formula:

$$R'O-G$$

in which R' denotes a saturated branched alkyl radical comprising from 12 to 44 carbon atoms, preferably from 16 to 36 and better still from 18 to 22, and the group G denotes a saccharide residue comprising from 5 to 6 carbon atoms, preferably a xylose residue.

In particular, the alkyl polyglucoside is an octyldodecyl xyloside such as the product sold under the name Fluidanov 20 X by the company SEPPIC in the form of a mixture consisting of 75% octyldodecanol and 25% octyldodecyl xyloside. The HLB value of this surfactant, calculated via the Davies method, is 3.425.

According to a particular embodiment, the surfactant(s) that are liquid at room temperature and at atmospheric pressure, with an HLB<8, which are suitable for use in the present invention are chosen from methylglucose dioleate and octyldodecyl xyloside.

The surfactant(s) that are liquid at room temperature and at atmospheric pressure, with an HLB<8 are generally present in the composition in an active material amount of between 0.001% and 1% by weight relative to the total weight of the composition, and preferably between 0.005% and 0.025% by weight relative to the total weight of the composition.

Additional Surfactants

The composition according to the invention may optionally comprise at least one additional surfactant other than the surfactants as defined previously, in one or other of the phases. When it contains an additional surfactant, this surfactant may be of the anionic, nonionic or amphoteric type, but it is preferably of the nonionic and/or anionic type. It is preferably present in the hydrophilic phase.

The amount of surfactant(s) as active material should be an amount such that the two phases remain separate at rest and do not mix to form an emulsion. This amount should generally be less than or equal to 1.5% by weight relative to the total weight of the composition. It may range, for example, from 0.01% to 1.5% by weight, preferably from 0.025% to 1% by weight and better still from 0.05% to 0.5% by weight relative to the total weight of the composition.

According to a preferred embodiment, the composition according to the invention comprises less than 2% by weight of additional surfactants relative to the total weight of the composition, preferably less than 1% by weight, and better still it is free of additional surfactants.

Among the additional nonionic surfactants, those that are particularly preferred are:

- polyoxyethylenated fatty esters of sorbitol such as the product sold under the name Tween 20 by the company ICI;
- polyoxyethylenated fatty alcohols such as the product sold under the name Remcopal 21912 AL by the company Gerland;
- polyoxyethylenated alkylphenols such as the product sold under the name Triton X 100 by the company Röhm & Haas;
- condensates of ethylene oxide and of propylene oxide such as those sold under the name Synperonic PE by the company ICI and in particular those referenced L 31, L 64, F 38, F 88, L 92, P 103, F 108 and F 127;
- fatty acid esters of glycerol or of polyglycerol, for instance glyceryl isostearate, poly(3-glyceryl) diisostearate or glyceryl caprylate;
- ethers of polyethylene glycol and/or of polypropylene glycol and of glycerol, such as glycereth-7, glycereth-26 and PPG-24 glycereth-24;
- esters derived from the reaction a) of fatty acids and b) of polyethylene glycol and/or polypropylene glycol glycerol ethers, for instance glycereth-2 cocoate or glycereth-25 PCA isostearate;
- fatty acid esters of sucrose other than those that are defined previously, comprising from 12 to 30 carbon atoms or in particular 14 to 20 carbon atoms, the said esters possibly comprising from 2 to 5 fatty chains, for instance sucrose distearate or sucrose tristearate;
- alkyl polyglucosides other than those that are defined previously, preferably those containing an alkyl group comprising from 6 to 30 carbon atoms and preferably from 8 to 16 carbon atoms and containing a hydrophilic (glucoside) group preferably comprising from 1.2 to 3 saccharide units. Examples that may be mentioned include decylglucoside (Alkyl-C9/C11-polyglucoside (1.4)), for instance the product sold under the name Mydol 10® by the company Kao Chemicals, the product sold under the name Plantaren 2000 UP® by the company Cognis, and the product sold under the name Oramix NS 10® by the company SEPPIC; caprylyl/capryl glucoside, for instance the product sold under the name Oramix CG 110® by the company SEPPIC; laurylglucoside, for instance the products sold under the names Plantaren 1200 N® and Plantacare 1200® by the company Cognis; cocoglucoside, for instance the product sold under the name Plantacare 818/UP® by the company Cognis; cetostearyl glucoside optionally as a mixture with cetostearyl alcohol, sold, for example, under the name Montanov 68 by the company SEPPIC, under the name Tego-Care CG90 by the company Goldschmidt and under the name Emulgade KE3302 by the company Henkel; arachidyl glucoside, for example in the form of the mixture of arachidyl alcohol and behenyl alcohol and arachidyl glucoside, sold under the name Montanov 202 by the company SEPPIC; cocoylethylglucoside, for example in the form of the mixture (35/65) with cetyl alcohol and stearyl alcohol, sold under the name Montanov 82 by the company SEPPIC; and mixtures thereof;
- polymeric emulsifiers such as hydrophobic-modified insulins, for example Inutec SP1 sold by the company Beneo Bio-Based Chemicals.

Among the anionic surfactants, mention may be made especially of:

- alkyl sulfates, alkyl ether sulfates and salts thereof, especially the sodium salts thereof, for instance the mixture of sodium laureth sulfate/magnesium laureth sulfate/sodium laureth-8 sulfate/magnesium laureth-8 sulfate, sold under the name Texapon ASV by the company Henkel; sodium lauryl ether sulfate (70/30 C12-14) (2.2 OE) sold under the names Sipon AOS 225 or Texapon N702 Pate by the company Henkel, ammonium lauryl ether sulfate (70/30 C12-14) (3 OE) sold under the name Sipon LEA 370 by the company Henkel; the ammonium (C12-C14) alkyl ether (9 OE) sulfate sold under the name Rhodapex AB/20 by the company Rhodia Chimie;
- alkyl sulfoacetates, such as that sold under the name Lathanol LAL by the company Stepan;
- alkyl sulfosuccinates, for example oxyethylenated (3 EO) lauryl alcohol monosulfosuccinate (70/30 C12/C14) sold under the names Setacin 103 Special and Rewopol SB-FA 30 K 4 by the company Witco, the disodium salt of a C12-C14 alcohol hemisulfosuccinate, sold under the name Setacin F Special Paste by the company Zschimmer Schwarz, the oxyethylenated (2 EO) disodium oleamidosulfosuccinate sold under the name Standapol SH 135 by the company Henkel, the oxyethylenated (5 EO) laurylamide monosulfosuccinate sold under the name Lebon A-5000 by the company Sanyo, the oxyethylenated (10 EO) disodium salt of lauryl citrate monosulfosuccinate sold under the name Rewopol SB CS 50 by the company Witco, and the disodium salt of ricinoleic acid monoethanolamide monosulfosuccinate sold under the name Rewoderm S 1333 by the company Witco;
- polypeptides that are obtained, for example, by condensation of a fatty chain onto the amino acids of cereals and especially of wheat and oat, for instance the potassium salt of hydrolyzed lauroyl wheat protein, sold under the name Aminofoam W OR by the company Croda, the triethanolamine salt of hydrolyzed cocoyl soybean protein, sold under the name May-Tein SY by the company Maybrook, the sodium salt of lauroyl oat amino acids, sold under the name Proteol Oat by the company SEPPIC, collagen hydrolysate grafted onto coconut fatty acid, sold under the name Geliderm 3000 by the company Deutsche Gelatine, and soybean proteins acylated with hydrogenated coconut acids, sold under the name Proteol VS 22 by the company SEPPIC;
- amino acid derivatives, for example among sarcosinates and especially acylsarcosinates such as the sodium lauroyl sarcosinate sold under the name Sarkosyl NL 97 by the company Ciba or sold under the name Oramix L 30 by the company SEPPIC, sodium myristoyl sarcosinate, sold under the name Nikkol Sarcosinate MN by the company Nikkol, sodium palmitoyl sarcosinate, sold under the name Nikkol Sarcosinate PN by the company Nikkol; alaninates, such as the sodium N-lauroyl-N-methylamidopropionate sold under the name Sodium Nikkol Alaninate LN 30 by the company Nikkol or sold under the name Alanone ALE by the company Kawaken, and the N-lauroyl-N-methylalanine triethanolamine, sold under the name Alanone ALTA by the company Kawaken; N-acylglutamates, such as the triethanolamine monococoylglutamate sold under the name Acylglutamate CT-12 by the company Ajinomoto, and the triethanolamine lauroylglutamate sold under the name Acylglutamate LT-12 by the company Ajinomoto; aspartates, such as the mixture of triethanolamine N-lauroylaspartate and triethanolamine N-myristoylaspartate, sold under the name Asparack LM-TS2 by the company Mitsubishi; glycine derivatives, such as sodium N-cocoylglycinate and potassium N-cocoylglycinate, such as the products sold under the names Amilite GCS-12 and Amilite GCK-12 by the company Ajinomoto;

sulfonates, for example, the α-olefinsulfonates, such as the sodium α-olefinsulfonate (C14-C16), sold under the name Bio-Terge AS-40 by the company Stepan, sold under the names Witconate AOS Protégé and Sulframine AOS PH 12 by the company Witco or sold under the name Bio-Terge AS-40 CG by the company Stepan, secondary sodium olefinsulfonate, sold under the name Hostapur SAS 30 by the company Clariant; or linear alkylarylsulfonates, such as the sodium xylenesulfonate sold under the names Manrosol SXS30, Manrosol SXS40 and Manrosol SXS93 by the company Manro;

isethionates, especially acylisethionates, such as sodium cocoylisethionate, such as the product sold under the name Jordapon CI P by the company Jordan.

Among the amphoteric or zwitterionic surfactants, mention may be made especially of:

alkylamido alkylamine derivatives such as N-disodium N-cocoyl-N-carboxymethoxyethyl-N-carboxymethylethylenediamine (CTFA name: Disodium cocoamphodiacetate) sold as an aqueous saline solution under the name Miranol C2M Conc NP by the company Rhodia Chimie; N-sodium N-cocoyl-N-hydroxyethyl-N-carboxymethylethylenediamine (CTFA name: sodium cocamphoacetate) and the mixture of coconut acid ethanolamides (CTFA name: Cocamide DEA);

betaines, for instance cocoylbetaine, such as the product sold under the name Dehyton AB-30 by the company Henkel, laurylbetaine, such as the product sold under the name Genagen KB by the company Clariant, oxyethylenated (10 EO) laurylbetaine, such as the product sold under the name Lauryl Ether (10 EO) Betaine by the company Shin Nihon Rica, or oxyethylenated (10 EO) stearylbetaine, such as the product sold under the name Stearyl Ether (10 EO) Betaine by the company Shin Nihon Rica;

alkylamidopropylbetaines and derivatives thereof, for instance the cocamidopropylbetaine sold under the name Lebon 2000 HG by the company Sanyo, or sold under the name Empigen BB by the company Albright & Wilson, the lauramidopropylbetaine sold under the name Rewoteric AMB12P by the company Witco, such as cocamidopropylbetaine, for instance the product sold under the name Tego Betaine by the company Goldschmidt;

imidazoline derivatives such as the product sold under the name Chimexane HD by the company Chimex.

Adjuvants

The composition according to the invention may also contain conventional cosmetic adjuvants or additives, which will be in one or other phase depending on their hydrophilic or lipophilic nature, for instance hydrophilic gelling agents, preserving agents and bactericides, dyes, softeners, buffers, humectants, UV-screening agents (or sunscreens), electrolytes such as sodium chloride or a pH regulator, for example citric acid or sodium hydroxide, and mixtures thereof.

Depending on the desired viscosity of the composition according to the invention, it is possible to incorporate therein one or more hydrophilic gelling agents. Examples of hydrophilic gelling agents that may be mentioned include modified or unmodified carboxyvinyl polymers, such as the products sold under the names Carbopol (INCI name: carbomer) by the company Noveon; polyacrylamides; optionally crosslinked and/or neutralized 2-acrylamido-2-methylpropanesulfonic acid homopolymers and copolymers, such as the poly(2-acrylamido-2-methylpropanesulfonic acid) sold by the company Clariant under the name Hostacerin AMPS (INCI name: ammonium polyacryldimethyltauramide); polysaccharide biopolymers such as xanthan gum, guar gum, alginates and celluloses, which may or may not be modified; and mixtures thereof. When they are present, these gelling agents must be introduced in an amount such that they do not modify the properties of the composition according to the invention. Lipophilic gelling agents that may be mentioned include alkene copolymers, for instance block copolymers of "diblock", "triblock" or "radial" type, of the polystyrene/polyisoprene or polystyrene/polybutadiene type, such as the products sold under the name Luvitol HSB® by the company BASF, of the polystyrene/copoly (ethylene-propylene) type, such as the products sold under the name Kraton® by the company Shell Chemical Co., or of the polystyrene/copoly(ethylene-butylene) type, and mixtures of triblock and radial (star) copolymers in isododecane, such as those sold by the company Penreco under the name Versagel®, for instance the mixture of butylene/ethylene/styrene triblock copolymer and of ethylene/propylene/styrene star copolymer in isododecane (Versagel M 5960).

The gelling agent may be present in an active material content ranging from 0.05% to 10% by weight and preferentially from 0.1% to 5% by weight relative to the total weight of the composition.

Preserving agents that may be used include any preserving agent usually used in the fields under consideration, for instance parabens, phenoxyethanol, chlorhexidine gluconate and polyhexamethylene biguanide hydrochloride (CTFA name: Polyaminopropyl biguanide). According to a preferred embodiment of the invention, the composition contains polyhexamethylene biguanide hydrochloride, alone or as a mixture with other preserving agents.

An example of a bactericide that may be used is a glyceryl mono($C_3$-$C_9$)alkyl or ($C_3$-$C_9$)alkenyl ether, the manufacture of which is described in the literature, in particular in E. Baer, H. O. L. Fischer—J. Biol. Chem. 140-397-1941. Among these glyceryl mono($C_3$-$C_9$)alkyl or ($C_3$-$C_9$)alkenyl ethers, use is preferably made of 3-[(2-ethylhexyl)oxy]-1,2-propanediol, 3-[(heptyl)oxy]-1,2-propanediol, 3-[(octyl)oxy]-1,2-propanediol and 3-[(allyl)oxy]-1,2-propanediol. A glyceryl mono($C_3$-$C_9$)alkyl ether that is more particularly preferred according to the present invention is 3-[(2-ethylhexyl)oxy]-1,2-propanediol, sold by the company Schulke & Mayr G.m.b.H. under the trade name Sensiva SC 50 (INCI name: Ethylhexylglycerin).

Among the softeners, mention may be made in particular of allantoin and bisabolol, planktons, and certain plant extracts, such as rose extracts and melilot extracts.

Electrolytes that may be mentioned include monopotassium or dipotassium phosphate, sodium chloride, magnesium sulfate and disodium EDTA.

The amount of salt(s) may range, for example, from 0 to 5% by weight, preferably from 0.1% to 2% by weight and better still from 0.5% to 1% by weight relative to the total weight of the composition.

According to the invention, the composition may also preferably comprise in the hydrophilic phase a dephasing agent in a proportion ranging, for example, from 0.025% to 5% by weight relative to the total weight of the composition.

Examples of dephasing agents that may be mentioned include alkyldimethylbenzylammonium chlorides as described in document EP-A-603 080, and especially benzalkonium chloride, and mixtures containing it; alkoxylated alkyl glucosides comprising a quaternary ammonium group and especially lauryl methyl gluceth-10 hydroxypropyldimonium chloride, as described in document EP-A-847 746; vinylpyrrolidone polymers and copolymers and especially the polyvinylpyrrolidone/hexadecene copolymer as described in document WO-A-99/56704; and mixtures thereof.

When such an agent is present, the ratio between the surfactant and the dephasing agent preferably ranges from 0.005/1 to 200/1 and better still from 0.01/1 to 120/1.

As active agents that may be used in the composition of the invention, examples that may be mentioned include enzymes (for example lactoperoxidase, lipase, protease, phospholipase, cellulases); flavonoids; moisturizers, such as protein hydrolysates; sodium hyaluronate; anti-inflammatory agents; oligomeric proanthocyanidins; vitamins such as vitamin A (retinol), vitamin E (tocopherol), vitamin C (ascorbic acid), vitamin B5 (panthenol), vitamin B3 (niacinamide), derivatives of these vitamins (in particular esters) and mixtures thereof; urea; caffeine; depigmenting agents such as kojic acid, hydroquinone and caffeic acid; salicylic acid and derivatives thereof; α-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, such as 2,4,4'-trichloro-2'-hydroxydiphenyl ether (or triclosan), 3,4,4'-trichlorocarbanilide (or triclocarban) and the acids indicated above, and in particular salicylic acid and derivatives thereof; tensioning agents; ceramides; essential oils; and mixtures thereof; and any active agent that is suitable for the final purpose of the composition.

The compositions described above may be conditioned, in a known manner, in a bottle with a single compartment. The user must then shake the bottle before pouring its contents onto a pad of cotton wool. The product may also be conditioned in a bottle of "pump-action bottle" type. According to a particular embodiment, it is a transparent container, generally made of polyethylene terephthalate (PET).

The composition according to the invention may be used for any topical application; it may especially constitute a cosmetic or dermatological composition. It may in particular be used for caring for, cleansing and/or removing makeup from the skin, the lips and/or the eyes, and also as a haircare composition.

Thus, a subject of the invention is also the cosmetic use of a cosmetic composition as defined above, for caring for, removing makeup from and/or cleansing the skin, the lips and/or the eyes, and/or for haircare.

A subject of the present invention is also a cosmetic process for removing makeup from, cleansing and/or caring for the skin, the lips and/or the eyes or the hair, characterized in that a cosmetic composition as defined above is applied to the skin, the lips and/or the eyes or the hair.

According to a preferred embodiment of the invention, the composition is a composition for cleansing and/or removing makeup from the skin, the lips and/or the eyes.

The examples below of compositions according to the invention are given as illustrations with no limiting nature. The amounts therein are given as weight percentages of starting material, unless otherwise mentioned. The names of the compounds are given as the chemical names or the INCI names.

EXAMPLES

Comparative Examples 1 to 3

The following compositions were prepared.

| Composition | 1 (invention) | 2 (invention) | 3 (comparative) |
|---|---|---|---|
| Disodium EDTA | 0.11 | 0.11 | 0.11 |
| Potassium phosphate | 0.46 | 0.46 | 0.46 |
| Dipotassium phosphate | 0.23 | 0.23 | 0.23 |
| Sodium chloride | 0.2885 | 0.2885 | 0.2885 |
| Isohexadecane | 16.92 | 16.92 | 16.92 |
| Dye | 0.06 | 0.06 | 0.06 |
| Fragrance | 0.02 | 0.02 | 0.02 |
| Polyaminopropyl biguanide (Cosmocil CQ from Arch Personal Care) | 0.29 | 0.29 | 0.29 |
| Hexylene glycol | 0.29 | 0.29 | 0.29 |
| Water | 55.97 | 55.97 | 55.85 |
| Isododecane | 25.25 | 24.9 | 25.36 |
| Decyl glucoside (Oramix NS 10 from SEPPIC) | — | — | 0.115 AM |
| Octyldodecanol (and) octyldodecyl xyloside (Fluidanov 20 X from SEPPIC) | — | 0.115 AM | — |
| Methylglucose dioleate (Glucate DO Emulsifier from Lubrizol) | 0.115 AM | — | — |

When the compositions are placed in a PET container, after shaking and rapid phase separation into two separate transparent phases, droplets may be seen, which adhere to the wall of the container, both on the fatty phase side and on the aqueous phase side, in the case of composition 3. The same test was performed with a composition according to Example 3 in which the decyl glucoside was replaced with Poloxamer 184 (sold by Faconnier). Droplets are also observed on the wall of the container after shaking and rapid phase separation.

There are no visible droplets on the walls of the container with compositions 1 and 2 in accordance with the invention.

Examples 4 to 6—Makeup-Removing Compositions According to the Invention

The following compositions were prepared.

| Composition | 4 |
|---|---|
| Oily phase: 43% of the composition | |
| Isohexadecane | 40 |
| Isododecane | 59.93 |
| Fragrance | 0.05 |
| Methylglucose dioleate (Glucate DO Emulsifier from Lubrizol) | 0.02 |
| Aqueous phase: 57% of the composition | |
| Water | 97 |
| Copper sulfate | 0.1 |
| Disodium EDTA | 0.2 |
| Potassium phosphate | 0.8 |
| Dipotassium phosphate | 0.4 |
| Sodium chloride | 0.5 |
| Polyaminopropyl biguanide (Cosmocil CQ from Arch Personal Care) | 0.5 |
| Hexylene glycol | 0.5 |

| Composition | 5 |
|---|---|
| Oily phase: 30% of the composition | |
| Undecane (and) tridecane (n-undecane/n-tridecane mixture in which n-undecane is predominant in the mixture, as prepared according to patent application WO 2008/155 059) | 10.90 |
| Octyldodecanol (and) octyldodecyl xyloside (Fluidanov 20 X from SEPPIC) | 0.1 |
| Isopropyl palmitate | 40 |
| Isododecane | 49 |
| Aqueous phase: 70% of the composition | |
| Water | 97.09 |
| Disodium EDTA | 0.2 |
| Potassium phosphate | 0.8 |
| Dipotassium phosphate | 0.4 |
| Sodium chloride | 0.5 |
| Polyaminopropyl biguanide (Cosmocil CQ from Arch Personal Care) | 0.5 |
| Citric acid | 0.005 |
| Arginine | 0.005 |
| Hexylene glycol | 0.5 |

| Composition | 6 |
|---|---|
| Oily phase: 30% of the composition | |
| Isopropyl palmitate | 39.91 |
| Isohexadecane | 50 |
| Isocetyl stearate | 10 |
| Octyldodecanol (and) octyldodecyl xyloside (Fluidanov 20 X from SEPPIC) | 0.09 |
| Aqueous phase: 70% of the composition | |
| Water | 98.425 |
| Sodium chloride | 1.2 |
| Dipotassium phosphate | 0.2 |
| Potassium phosphate | 0.07 |
| Polyaminopropyl biguanide (Cosmocil CQ from Arch Personal Care) | 0.1 |
| Arginine | 0.005 |

Compositions 4 to 6 were prepared in the following manner:

Everything is performed without heating. The starting materials of the aqueous phase are added one by one and then the beaker containing them is stirred magnetically until homogenization and dissolution are complete. The same is done for the starting materials of the fatty phase. The two phases are then placed in contact, without stirring.

Each of the compositions 4 to 6 described above is shaken before use to emulsify the two oily and aqueous phases temporarily, and they are then applied to a pad of cotton wool and then onto the face and/or the eyes to remove makeup. The product has good sensory properties and good makeup-removing efficacy is observed. After use, the product separates rapidly into two transparent phases, having a perfectly sharp interface and with no appearance of droplets that remain attached to the walls of the transparent container.

The invention claimed is:

1. A composition consisting of an aqueous phase and an oily phase, which are separate and transparent, comprising at least one surfactant that is liquid at room temperature (20-25° C.) and at atmospheric pressure (760 mmHg or $1.013\times10^5$ Pa), with an HLB<8 and chosen from fatty acid esters of sugar and alkyl polyglucosides, at least one branched alkane comprising from 8 to 18 carbon atoms, and from 0 to 4% by weight of silicone oils relative to the total weight of the composition.

2. The composition according to claim 1, in which the at least one surfactant that is liquid at room temperature and at atmospheric pressure, with an HLB<8 comprise one or more linear or branched, saturated or unsaturated hydrocarbon-based chains, comprising from 11 to 44 carbon atoms.

3. The composition according to claim 1, in which the fatty acid ester(s) of sugar are monoesters or polyesters of fatty acid and of sugar or of alkyl sugar, which esters may be oxyalkylenated, or polyglycerolated.

4. The composition according to claim 3, in which the fatty acid ester(s) of sugar are chosen from monoesters or diesters of a C11-C22, bearing a linear or branched, saturated or unsaturated hydrocarbon-based chain, comprising from 11 to 22 carbon atoms, and of sugar or of alkyl sugar.

5. The composition according to claim 3, in which the fatty acid ester(s) of sugar are chosen from fatty acid esters of sucrose, maltose, glucose, fructose, mannose, galactose, arabinose, xylose, lactose, trehalose or methylglucose.

6. The composition according to claim 1, in which the fatty acid ester(s) of sugar result from the reaction of a fatty acid whose fatty unit comprises an unsaturated linear hydrocarbon-based chain comprising from 12 to 24 carbon atoms, and of a ($C_1$-$C_4$ alkyl) sugar.

7. The composition according to claim 1, in which the fatty acid ester of sugar is methylglucose dioleate.

8. The composition according to claim 1, in which the alkyl polyglucoside(s) are chosen from the compounds having the following general formula:

$$RO\text{-}(G)_a$$

in which R denotes a saturated or unsaturated, linear or branched hydrocarbon-based chain comprising from 12 to 44 carbon atoms, the group G denotes a saccharide residue comprising from 5 to 6 carbon atoms and a is a number ranging from 1 to 10.

9. The composition according to claim 8, in which the saccharide residue is chosen from glucose, dextrose, saccharose, fructose, galactose, maltose, maltotriose, lactose, cellobiose, mannose, ribose, dextran, talose, allose, xylose, levoglucan, cellulose, starch and methylglucose.

10. The composition according to claim 1, in which the alkyl polyglucoside(s) are chosen from the compounds having the following formula:

R'O-G in which R' denotes a saturated branched alkyl radical comprising from 12 to 44 carbon atoms, and the group G denotes a saccharide residue comprising from 5 to 6 carbon atoms.

11. The composition according to claim 8, in which the alkyl polyglucoside is octyldodecyl xyloside.

12. The composition according to claim 1, in which the branched alkane(s) comprising from 8 to 18 carbon atoms are chosen from $C_8$-$C_{18}$ isoalkanes.

13. The composition according to claim 1, in which the branched alkane(s) comprising from 8 to 18 carbon atoms are present in the composition in an amount at least equal to 40% by weight relative to the total weight of the oily phase.

14. A cosmetic process which comprises applying a composition according to claim 1 to hair.

15. A cosmetic process for removing makeup from, cleansing and/or caring for the skin, the lips and/or the eyes, in which a composition according to claim 1 is applied to the skin, the lips and/or the eyes.

16. The composition according to claim 2, in which the fatty acid ester(s) of sugar are monoesters or polyesters of fatty acid and of sugar or of alkyl sugar, which esters may be oxyalkylenated, or polyglycerolated.

17. The composition according to claim 4, in which the fatty acid ester(s) of sugar are chosen from fatty acid esters of sucrose, maltose, glucose, fructose, mannose, galactose, arabinose, xylose, lactose, trehalose or methylglucose.

18. The composition according to claim 3, in which the fatty acid ester(s) of sugar are chosen from fatty acid esters of sucrose, glucose or methylglucose.

19. The composition according to claim 3, in which the fatty acid ester(s) of sugar are chosen from fatty acid esters of methylglucose.

20. The composition according to claim 2, in which the fatty acid ester(s) of sugar result from the reaction of a fatty acid whose fatty unit comprises an unsaturated linear hydrocarbon-based chain comprising from 12 to 24 carbon atoms, and of a ($C_1$-$C_4$ alkyl) sugar.

* * * * *